(12) United States Patent
Lee et al.

(10) Patent No.: US 7,365,533 B2
(45) Date of Patent: Apr. 29, 2008

(54) MAGNETO-OPTIC REMOTE SENSOR FOR ANGULAR ROTATION, LINEAR DISPLACEMENTS, AND EVALUATION OF SURFACE DEFORMATIONS

(75) Inventors: Seong-Jae Lee, Ames, IA (US); Sang-Hoon Song, Ames, IA (US); Yevgen Melikhov, Penarth (GB); Choon-Mahn Park, Seoul (KR); Hans Hauser, Vienna (AT); David Jiles, Glamorgan (GB)

(73) Assignee: Iowa State University Research Foundation, Inc., Ames, IA (US)

( * ) Notice: Subject to any disclaimer, the term of this patent is extended or adjusted under 35 U.S.C. 154(b) by 105 days.

(21) Appl. No.: 11/459,157

(22) Filed: Jul. 21, 2006

(65) Prior Publication Data
US 2007/0057668 A1   Mar. 15, 2007

Related U.S. Application Data

(60) Provisional application No. 60/701,794, filed on Jul. 22, 2005.

(51) Int. Cl.
*G01R 33/032* (2006.01)
*G02F 1/09* (2006.01)

(52) U.S. Cl. .................... 324/244.1; 359/280; 359/281

(58) Field of Classification Search ........... 324/207.11, 324/207.13, 207.22, 207.24, 207.25, 207.26, 324/244.1, 244, 260, 96–97; 359/280–284, 359/484; 250/225
See application file for complete search history.

(56) References Cited

U.S. PATENT DOCUMENTS 6,521,884 B1 * 2/2003 Breda .................... 250/225

OTHER PUBLICATIONS

Y. S. Didosyan et al., Application of orthoferrites for light spot position measurements, paper, May 1, 2000, 3 pages, pp. 7079-7081, vol. 87, No. 9.
Yuri S. Didosyan et al., Magneto-Optical Current Sensor by Domain Wall Motion in Orthoferrites, paper, Apr. 2000, 5 pages, vol. 49, No. 1.
Yuri S. Didosyan et al., Magnetooptic Switch Based on Domain Wall Motion in Orthoferrites, paper, Sep. 2002, 3 pages, pp. 3243-3245, vol. 38, No. 5.
E. Hristoforou et al., Mechanical Sensors Based on Re-Entrant Flux Reversal, paper, Sep. 1992, 3 pages, vol. 28, No. 5.
Y. S. Didosyan et al, Magneto-optical rotational speed sensor, paper, 2003, 3 pages, pp. 168-171, Sensors and Actuators A 106.
Y. S. Didosyan et al., Magnetic field sensor by orthoferrites, paper, 1997, 5 pages, Sensors and Actuators A 59.
K. B. Rochford et al., Magneto-Optic Sensors Based on Iron Garnets, paper, Sep. 1996, 5 pages, pp. 4113-4117, vol. 32, No. 5.
M. Klank et al., Sensitive magneto-optical sensors for visualization of magnetic fields using garnet films of specific orientations, paper, Dec. 1, 2002, 5 pages, vol. 92, No. 11.

* cited by examiner

*Primary Examiner*—Bot LeDynh
(74) *Attorney, Agent, or Firm*—Reinhart Boerner Van Deuren P.C.

(57) ABSTRACT

A system and method to detect angular rotation, linear displacement and/or surface deformations is presented. The method is based on the ability of a linear polarized light to interact with magnetic materials and to change its polarization angle due to Faraday effect. A basic structure of the system consists of a magneto-optic (MO) film with a two-domain structure and a single domain wall which are generated by gradient magnetic field produced by opposite polarity permanent magnets placed near the film. An AC magnetic field applied perpendicular to the MO film surface causes the magnetic domain wall in the MO film to oscillate at the same frequency. This leads to a detected output AC modulated signal. By measuring the temporal changes in this signal, information on angular rotation, linear displacement and/or surface deformation can be obtained.

19 Claims, 4 Drawing Sheets

FIG. 1
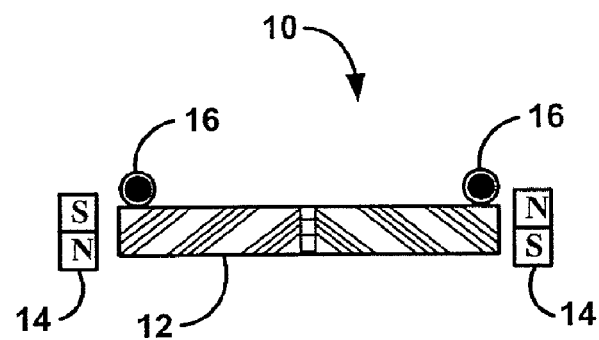
FIG. 2a  FIG. 2b  FIG. 2c
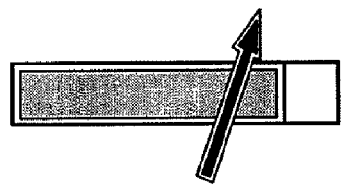 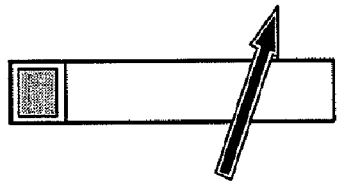 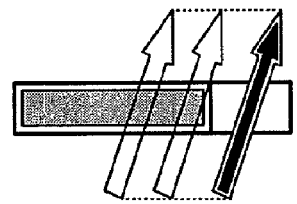
FIG. 3
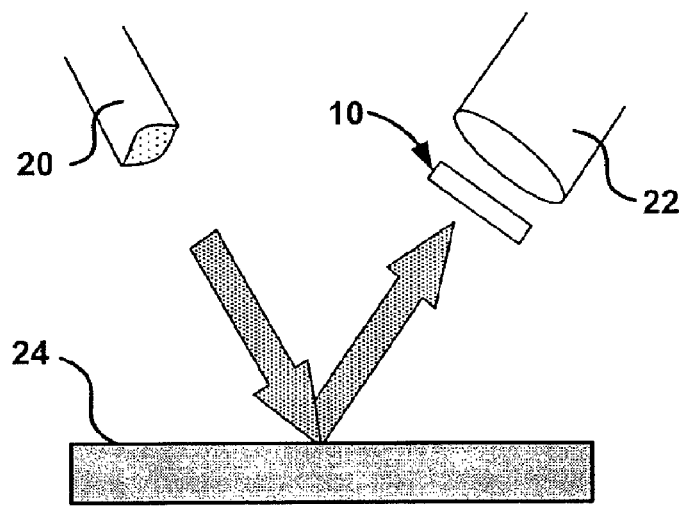

Time (f=50 Hz, T=0.02 sec)

Time

Time (f=40 Hz, T=0.025 sec)

MAGNETO-OPTIC REMOTE SENSOR FOR ANGULAR ROTATION, LINEAR DISPLACEMENTS, AND EVALUATION OF SURFACE DEFORMATIONS

CROSS-REFERENCE TO RELATED PATENT APPLICATIONS

This patent application claims the benefit of U.S. Provisional Patent Application No. 60/701,794, filed Jul. 22, 2005, the entire disclosure which is incorporated by reference in its entirety herein.

STATEMENT REGARDING FEDERALLY SPONSORED RESEARCH AND DEVELOPMENT

This invention was made in part with Government support under Grant Numbers NAG-1-02098 awarded by the National Aeronautical and Space Administration. The Government may have certain rights in this invention.

FIELD OF THE INVENTION

The subject matter generally relates to displacement sensors, and more particularly, to displacement sensors that detect angular rotation, linear displacement and microscopic surface and subsurface deformation in materials.

BACKGROUND

Surface deformation caused by sub-surface and internal defects can often be the cause of failure in structural components. Small and reliable sensors for remote detection of angular and/or spatial displacements of a material are important for many practical applications. For example, accurate detection of cracks in aircraft is important.

Various nondestructive evaluation (NDE) techniques have been developed for detecting and evaluating defects including surface discontinuities, surface flaws, voids, and cracks on the surface or in the body of materials. Most NDE techniques have been developed for investigating metallic materials because most load bearing parts in industry are made of metallic materials. Metallic materials can be categorized in magnetic and nonmagnetic materials depending on their magnetic permeability. For magnetic metallic materials such as steel, techniques such as eddy current, magnetic flux leakage, magnetic Barkhausen noise, and magnetic particle inspection can be employed. For nonmagnetic materials, dye penetrant, radiography, and ultrasonic techniques can be used.

The eddy current technique can be used for both magnetic and nonmagnetic materials, but the materials under investigation must have sufficient electrical conductivity to allow electromagnetically induced currents to be generated in order for the eddy current technique to be viable. The other techniques described above do not work on both magnetic and non magnetic metallic materials.

Compared with the development of magnetic and electromagnetic techniques, the application of optical methods for NDE has been less widespread. Optical methods have the advantage that they can provide inspection without needing a direct contact with the test material. Any changes on the surface can be monitored by a reflected light beam signal. This signal can be detected by a photodiode or a CCD. In addition to the capability for remote measurement of defects, optical methods provide high stability with respect to electromagnetic interference, high spatial resolution and the capability of performing over a wide frequency range.

The existing magneto-optic technique for NDE applications employs magneto-optic film that can sense stray magnetic fields from a surface defect. The technique is performed by placing a magneto-optic film in close proximity to the surface of the material. Magnetic leakage fields from a surface defect cause rearrangement of domain structure in the magneto-optic film, giving rise to contract in the domain images of the magneto-optic film which are indicative of defects in the surface. The problem with this technique is that it is insufficiently sensitive for surface deformation caused by sub-surface and internal defects (i.e., micro-scale surface deformation) due to negligible magnetic flux leakage fields. Furthermore, this technique is not applicable to non-conducting materials (e.g., ceramics, polymer-matrix composites, etc.) due to the absence of magnetic flux leakage fields emanating from the non-conducting materials.

BRIEF SUMMARY

Described herein are, among other things, embodiments of a technique applicable to non-conducting materials. These and other advantages, as well as additional inventive features, will be apparent from the description provided herein.

In one aspect, provided is a magneto-optic sensor technique that provides the capability for the estimation of angular rotation, linear displacement and for the evaluation of surface deformations for all types of materials: magnetic, non-magnetic, conducting, and non-conducting materials. The technique uses a combination of laser beam technology and magnetics to remotely detect surface deformation. The modulated AC output signals as a function of time are very sensitive to the change in intensity of reflected light. The technique can detect internal defects that are not visible by measurement of surface. For example, it can enhance aircraft safety by evaluation of deformations on the surface of the aircraft skin and other objects by remotely detecting surface changes to a level below 0.002 degrees.

In another aspect, the invention provides a system to detect angular rotation, linear displacement and/or deformations that consists of a laser, one or two magneto-optic ("MO") films, one or two excitation coils, two or four permanent magnets, an analyzer, and a photodetector. During operation, deformed surfaces on the sample can be easily detected by monitoring the changes of the signal from those of an undeformed surface.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings:

FIG. 1 is a schematic diagram of a magneto-optic polarizer changer (MOPC) for a magneto-optic sensor constructed in accordance with the teachings of the present invention;

FIG. 2(*a*) shows the change of the rotation angle in a MOPC due to domain wall movement caused by the external field;

FIG. 2(b) shows the change of the rotation angle in a MOPC due to domain wall movement caused by the external field;

FIG. 2(c) shows the change of the rotation angle by changing the position of the light beam;

FIG. 3 is a graph illustrating a magneto-optic sensor based on a single MOPC when only a reflected beam goes through the MOPC;

Figure 4:
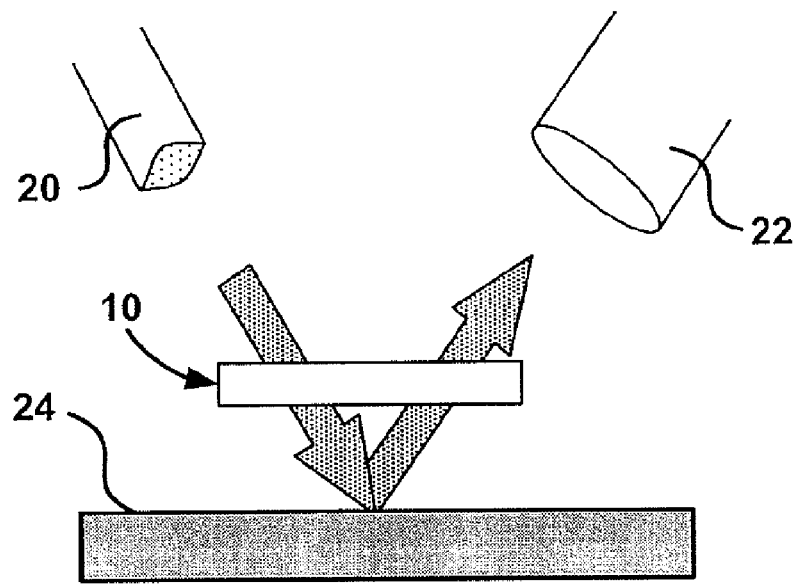
FIG. 4 is a graph illustrating the magneto-optic sensor of FIG. 3 when both the incident and reflected light beams go through the MOPC.

While the subject matter will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION

Described herein is a magneto-optic (MO) nondestructive evaluation (NDE) technique that is based on the periodically modulated Faraday Effect for detecting surface deformation created by sub-surface or internal defects. This magneto-optic technique provides a non-contact method for investigation of materials which enables a remote sensor system to be developed. The technique has been applied to detection of surface defects, weak magnetic fields, electric currents, and rotational speed. Remote evaluation of microscopic surface deformation is possible with the invention because the technique does not require close contact between the sample surface and the magneto-optic sensor film in order to perform the evaluation of surface deformation. The technique was found to provide sufficient sensitivity for a small deformation by using simulated surface deformation by rotation of 0.002 degrees of a test sample surface. The angle of 0.002 degrees is the difference between the light reflections from an undeformed surface and the deformed surface, which can be a measure of surface deformation. The invention utilizes domain wall motion in a transparent MO thin film for evaluation of surface deformation created by sub-surface and internal defects. The invention is suitable for both conducting and non-conducting specimens. The surface of the test sample should be sufficiently reflective.

The technique is based on the magneto-optic Faraday Effect that occurs when a linearly plane polarized light beam interacts with a transparent magnetic material, such as a garnet. The magnitude of the Faraday rotation is dependent on the magneto-optic properties of the MO material and the path length of the light through the MO material with respect to the magnetization vector. In the polar geometrical configuration, where directions of the applied magnetic field B and incident linearly plane polarized light beam are perpendicular to the surface of the MO material, the magnitude of Faraday rotation is given by $\Phi_F = V \cdot d \cdot B$ where V is the Verdet constant, d is the thickness of the MO film, and B is the magnitude of the magnetic flux density in the film.

The magneto-optic film has a magnetic anisotropy with its easy axis of magnetization normal to the MO film surface and a hard axis of magnetization lying in the surface of the MO. Therefore, a small magnetic field perpendicular to a surface plane can easily cause re-arrangement of domain structures in the MO film.

Turning now to FIG. 1, the conception of the magneto-optic polarizer changer (MOPC) shall be described. Each magneto-optic polarizer changer (MOPC) 10 consists of the magneto-optic garnet film 12, two hard ferrite permanent magnets 14 with opposite polarity and an AC excitation coil 16. Two permanent magnets 14 are positioned close to the garnet film 12 such that they generated a uniform magnetic field gradient ($H_{PM}$) within the garnet film. As a result of this magnetic field gradient, a stable two-domain structure with opposite directions of magnetization and a single domain wall (DW) is formed. When there is no applied AC magnetic field, the equilibrium position of the DW is at the center of the film halfway between the two permanent magnets. The current in the coil 16 placed on top of the MO film 12 is modulated periodically (e.g., sinusoidal, sawtooth or other waveform, any of which is referred to herein as AC), which generates an additional magnetic field $H_{AC}(\omega t)$, which is perpendicular to the surface of the MO film 12. This field induces oscillation of the domain wall with the same angular frequency.

$H_{PM}$ should be larger than the pinning field of the MO film. When there is no applied AC magnetic field, the equilibrium position of the DW is at the center of the film halfway between the two permanent magnets. An AC magnetic field is applied perpendicular to the surface of the MO film using an excitation coil to which a periodical current is applied. The periodical magnetic field generated by this excitation coil has a function of $H_{AC} = Ho \, f(\omega t)$ where $f(\omega t)$ is a periodic function (sinusoidal, sawtooth, etc.) where $\omega 0$ is the applied angular frequency. This AC magnetic field causes the magnetic domain wall in the MO film to oscillate with the same angular frequency $\omega$. In this case, the Faraday rotation has the form, $\Phi_F = V \cdot d \cdot H_o f(\omega t)$. With the addition of $H_{AC}$ to $H_{PM}$, the equilibrium position of the domain wall shifts to where the sum of the two magnetic fields is zero.

If a polarized light goes through the MOPC 10, its polarization will change depending on the current position of domain structure due to magneto-optical Faraday Effect. As only two domains exist in this domain structure, the polarization rotation angle could take two extreme values only with a gradual change between them when the domain wall spreads directly under the light beam pass. As domain wall moves under the external field, the rotation angle will change with time as seen in FIGS. 2a and 2b. Another way of changing the rotation angle is by changing the position of the light beam as shown in FIG. 2c.

Figure 5:
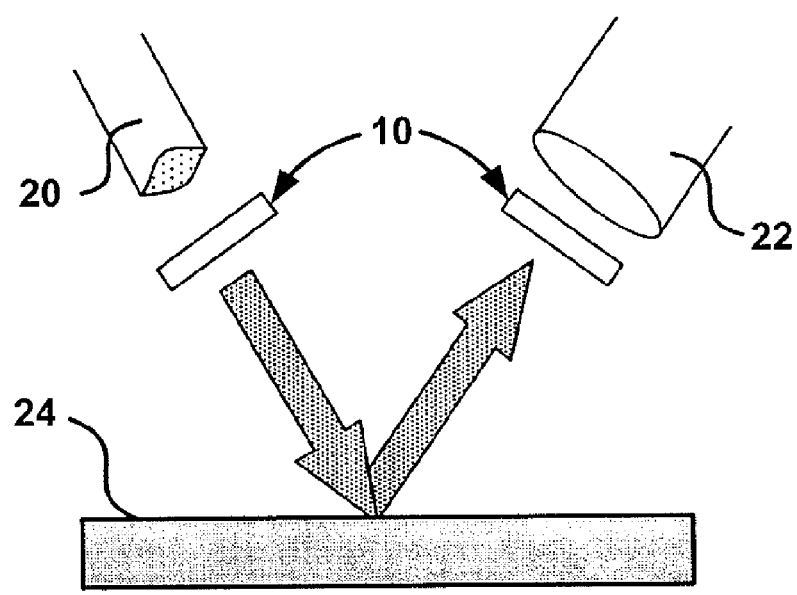
FIG. 5 is a graph illustrating a magneto-optic sensor based on two MOPCs (the incident light beam goes through one MOPC and the reflected light beam goes through the other MOPC)

An embodiment of the present sensor with different MO sensor geometries is illustrated in FIG. 3, FIG. 4, and FIG. 5. The system consists of a He—Ne laser 20, one or more (e.g., two) MOPCs 10, and an analyzer 22 having a photodetector. Other light beam sources may be used. During operation, angular rotated, linear displaced or deformed surfaces on the sample 24 can be easily detected by monitoring the changes of the signal from those of an unmoved or undeformed surface. The sensor system can also capture surface deformations and these can be recorded digitally for further numerical analysis. Sub-surface defects can be detected from the measurements of surface deformation employing this technique.

In the sensors shown, the periodically modulated Faraday rotation in one or more MOPCs leads to a periodically modulated signal detected by a photodetector. As a result of these two magnetic fields (one is oscillatory and the other one is stable), the periodically modulated output signal is very sensitive to the position of the reflected light beam path due to the movement of domain wall(s) in the MOPC(s). The maximum output signal occurs when positive rotation angle from one reflected light beam (if one MOPC is present) or positive rotation angles from both incident and reflected light beams (if two MOPC are present) are summed up. The minimum output signal occurs when the negative rotation angle from one reflected light beam (if one MOPC is present) or two negative rotation angles from both incident and reflected light beams (if two MOPC are present) are summed up. A flat region (e.g., a shoulder) occurs in the case of the MO sensors of FIG. 4 and FIG. 5 when the rotational angles from incident and reflected light beams have opposite sign. A systematic change of the width of the flat region occurs as the angle of deflected light beam increases. Measurement of the reflection angle of the light beam is converted into measurement of the temporal length of the distinctive flat region (e.g., shoulder) of the signal relative to the rest of the detected signal. This measurement can be done with higher accuracy than signal amplitude measurements and the results are largely independent of the reflectance of the sample. By measuring the changes of the width of the flat region in the intensity versus time waveform, information on surface deformation can be obtained.

The MO sensor system (for sensing angular, sensing linear displacements or for sensing surface deformations) based on one MOPC (when only the reflected light beam goes through the MOPC as shown in FIG. 3) provides a completely remote way of sensing. The MOPC can be put as far as necessary from the investigated specimen. Any changes (angular rotation, linear movement or surface deformations) of the specimen will cause the change in the position of the impediment of the reflected light beam into the MOPC. This will cause the changes in the behavior of the angle of polarization and these changes are detected by the analyzer with the photodetector. Note that even when there is no flat region (shoulder) in the output signal, there will be temporal changes in the output signal.

The same sensitivity can be achieved if both incident and reflected light beams go through one MOPC as shown in FIG. 4. This sensor can not be completely remote because both incident and reflected beams have to go through the MOPC and this influences the angle of incident and/or distance where to put the MOPC, and the dimensions of the MOPC.

The MO sensor with two MOPCs as shown in FIG. 5 provides the ability to separately change either periodical functions which drive the coils of each MOPCs and/or angular frequencies of these functions. This ability allows manual or automatic control of the output on the photodetector with analyzer. This type of the sensor is also completely remote and can be easily converted into the MO sensors of FIGS. 3 and 4. For example, if the current for the excitation coil of the MOPC for the incident light beam is constant, this will repeat the response of the sensor of FIG. 3. If the current waveforms and their frequencies of both MOPCs are the same, it will become the MO sensor of FIG. 4.

As an example, further on we consider the response of the MO sensor presented in FIG. 4.

Figure 6:
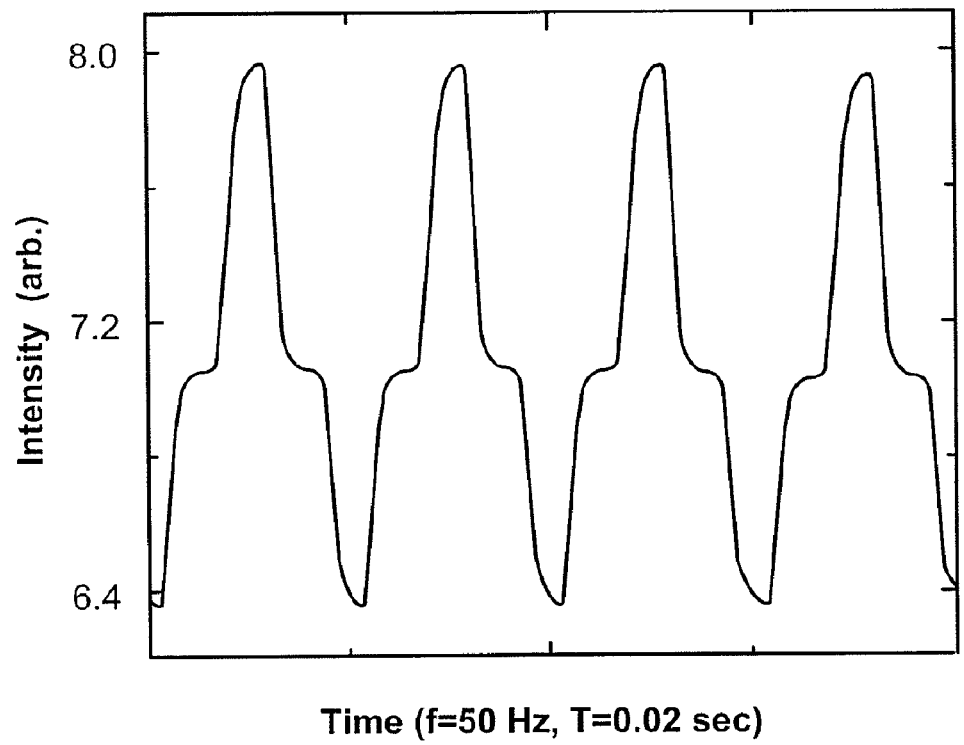
FIG. 6 is a graph illustrating the intensity of a light beam without surface rotation detected by the magneto-optic sensor of FIG. 4.

During operation, a polarized light beam generated by the He—Ne laser 20 passes through the MO film 12. In the discussion that follows, the MO film 12 is a bismuth-doped iron garnet $(Bi,Tm)_3(Fe,Ga)_5O_{12}$ (thickness~3 μm) grown on a thin substrate of gadolinium gallium garnet (GGG). The thickness of the GGG substrate was 0.5 mm. It is noted that other types of MO film may be used with the invention. The bismuth-doped iron garnet film had a large specific Faraday rotation, $\theta_F$, up to 2.3 degrees/μm of thickness. The domain walls in the bismuth-doped garnet MO film are activated at a threshold magnetic field of 0.1-0.3 mT. A 50 Hz frequency AC field H is produced by a solenoid 16 and applied to the surface of the MO film 12, which caused the domain wall between oppositely magnetized domains to move. Consequently, when a periodical AC current is applied to the solenoid coil 16, the signal detected at the photodetector 22 is also periodical as illustrated in FIG. 6.

Two hard ferrite magnets (remanence $B_r$=0.350 T and coercivity $H_c$=260 kA/m) with opposite polarity are arranged as shown in FIG. 1. Other types of magnets may be used. The magnets 14 are used for generating a suitable magnetic field gradient within the MO film 12. In the description that follows, the distance between the two permanent magnets 14 was 15 mm and the distance between sample and the MO sensor was 100 mm. Other distances may be used. As a result of the field gradient generated by the magnets 14, a two domain structure with opposite direction of magnetization is formed. The equilibrium position of the domain wall is located where the strengths of the $H_{PM}$ and the AC field, $H_{AC}$, are equal and opposite, that is $H_{PM}+H_{AC}=0$. Under the action of an AC field, the domain wall oscillates about the equilibrium position.

Figure 7:
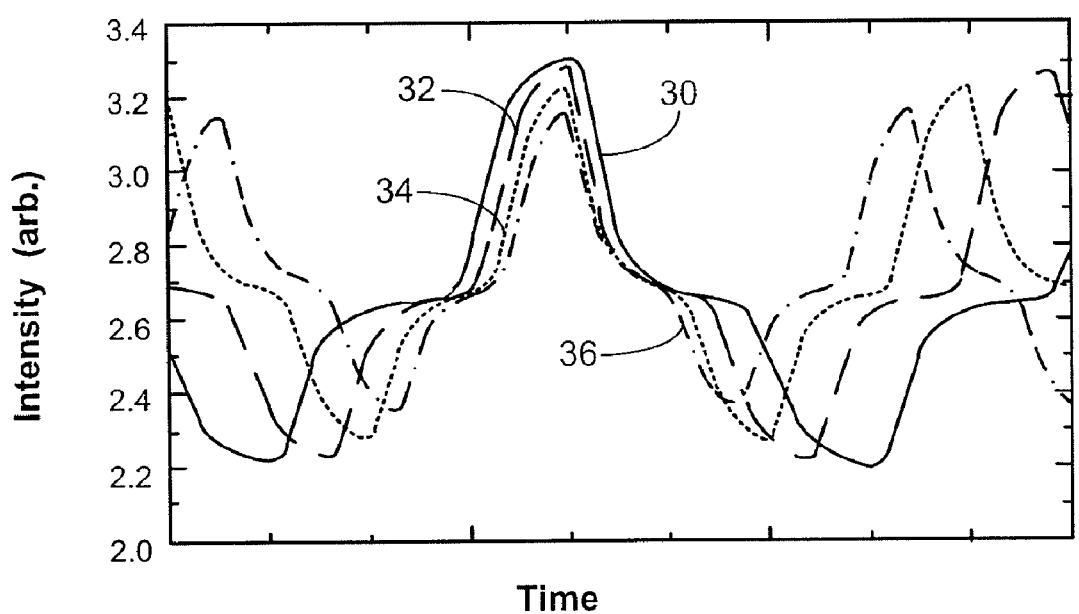
FIG. 7 is a graph illustrating the variation of the intensity of the reflected light beam as the frequency of the applied frequency changes from 40 Hz to 70 Hz.
Figure 8:
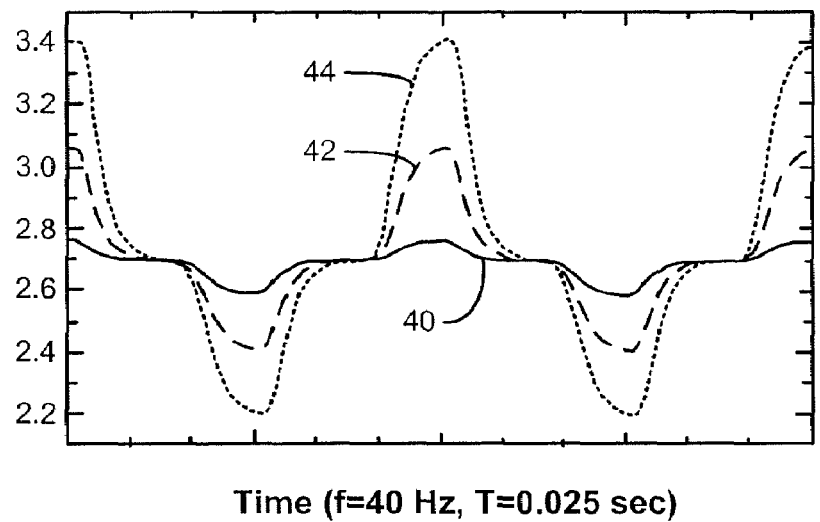
FIG. 8 is a graph illustrating the variation of the intensity of the reflected light beam as the applied peak to peak voltage of the coil current of the magneto-optic sensor increases.

The applied frequency of the AC magnetic field was 40 Hz. The variation of signal shape as the frequency of the applied AC magnetic field changes from 40 Hz to 70 Hz with a step of 10 Hz is shown in FIG. 7. Line 30 is the signal at 40 Hz, line 32 is the signal at 50 Hz, line 34 is the signal at 60 Hz, and line 36 is the signal at 70 Hz. The size of the flat region between the positive output signal and the negative output signal increases as the period of the AC excitation field increases. Changes of detected signal as the magnitude of the applied voltage, $V_{pp}$, to the solenoid current coil increases is shown in FIG. 8 at a frequency of 40 Hz. Line 40 is the signal with a Vpp of 0.4V, line 42 is the signal with a Vpp of 0.45V, and line 44 is the signal with a Vpp of 0.5 V. It can be seen that a 10% increase of the applied voltage leads to about 50% increase of the intensity detected by the photodetector 22.

Simulations to determine how surface deformations are detected at the photodetector 22 were performed. Surface deformation was simulated by mounting an aluminum mirror on a rotator providing pure rotational motion of $7 \times 10^{-3}$ degrees per graduation. The incident light beam passed through the solenoid coil 16 and between the two permanent magnets 14, was reflected from the surface of the sample and was detected at the photodetector 22. For simulation of surface deformation, rotations of 0.02 and 0.04 degrees of a sample were made and the intensity of the detected light beam for each rotation was measured.

The intensity of the light beam detected by the photodetector 22 has the waveform of a half positive output signal and a half negative output signal separated by a flat region between the two output signals as shown in FIG. 6. The positive change in intensity of the output signal occurs while the up-domain expands to the position where it covers both the incident and reflected light beam paths. The negative change in intensity of the output signal occurs while the down-domain expands to the position where it covers both the incident and reflected light beam paths. The line between the two opposite signals appears when the incoming light beam path is in the one domain and the reflected light beam path is in the other domain. The change in intensity in this case is zero due to the cancellation of Faraday rotations in the MOPC.

Figure 9:
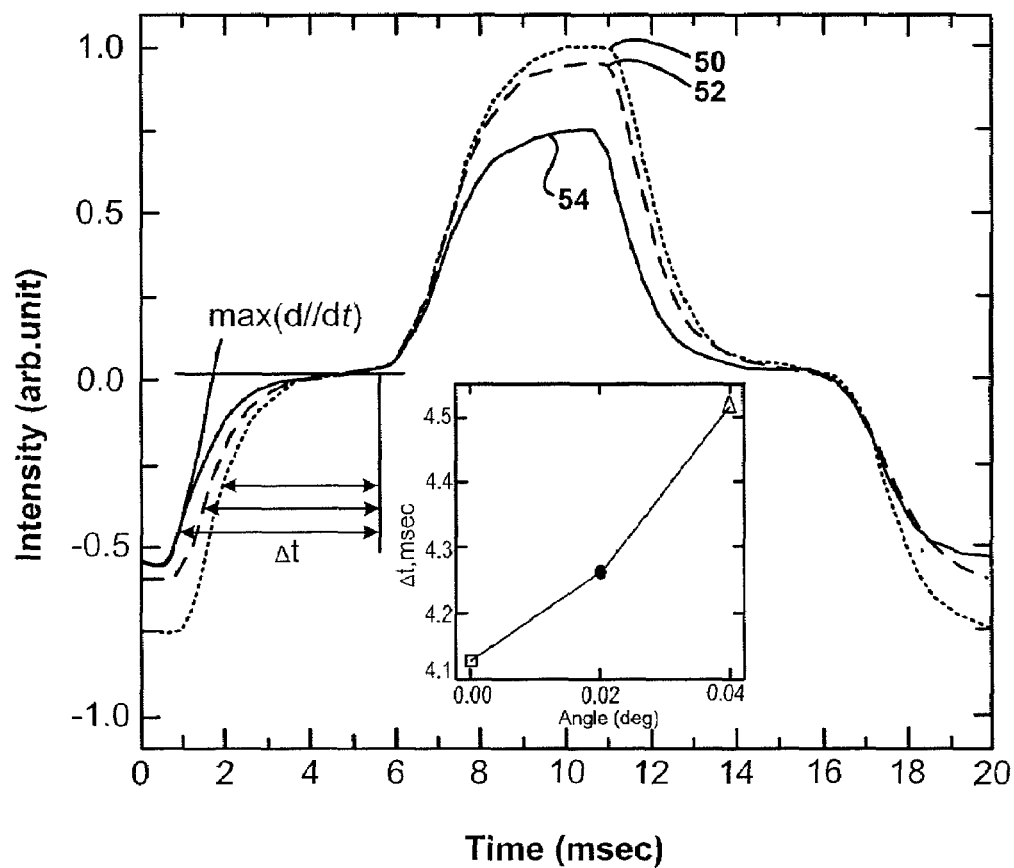
FIG. 9 is a graph illustrating the measured intensity of the reflected light beam for rotations of the surface of a sample.

Measured intensities for rotations of the surface of aluminum by 0.00, 0.02, and 0.04 degrees are plotted in FIG. 9. The dotted line (designated with reference numeral 50) in FIG. 9 represents the intensity of the signal without rotation of the sample. The dashed line (designated with reference numeral 52) shows the intensity of the detected signal with sample rotation of 0.02 deg. The solid line (designated with reference numeral 54) shows the intensity of the signal with sample rotation of 0.04 deg. From the measured data, it can be seen that the detected intensities are sensitive to the rotation of the surface of the test specimen. As shown in FIG. 9, a systematic increase of the width of the flat region occurs as the angle of deflected light beam increases. Therefore, measurement of the reflection angle of the light beam can be converted into measurement of the temporal length of the distinctive flat region (e.g., shoulder) of the signal relative to the rest of the detected signal. This measurement can be done with higher accuracy than signal amplitude measurements and the results are largely independent of the reflectance of the sample. For example, a change in the intensity due to an off-centered laser beam can alter the magnitude of the measured maximum intensity level, but this change does not provide any pattern useful for surface rotation detection since any background intensity changes could alter the maximum intensity level. By measuring the temporal changes in the output signal, information on angular rotation, linear displacement and/or surface deformation can be obtained. The measurement of the width of the flat region is independent on variations in reflected intensity from the surface of the material and can be made with high accuracy. By measuring the changes of the width of the flat region in the intensity versus time waveform, information on surface deformation can be obtained. Note that some reflection is necessary. In the case where the reflected light intensity is weak, the signal-to-noise-ratio will be affected.

From the foregoing, it can be seen that the MO sensor technique of the invention allows for the estimation of angular rotation, linear displacement and/or evaluation of surface deformations for all types of materials: magnetic, non-magnetic, conducting, and non-conducting materials. This technique uses a combination of laser beam technology and magnetics to remotely detect surface deformation. The modulated AC output signals as a function of time as described herein are very sensitive to the change in intensity of reflected light. The technique can detect internal defects that are not visible by measurement of surface. For example, it can enhance aircraft safety by evaluation of deformations on the surface of the aircraft skin and other objects by remotely detecting surface changes to a level below 0.002 degrees.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A magneto-optic sensor for remote evaluation of surface deformations on a magnetic or non-magnetic surface comprising:
    a polarized light beam source adapted to shine an incident light beam on the magnetic or non-magnetic surface;
    at least one magneto-optic polarizer changer adapted to receive reflected light from the magnetic or non-magnetic surface, each of the at least one magneto-optic polarizer changer comprising:
        a magneto-optic film;
        at least two permanent magnets having an opposite polarity with each other positioned to generate a magnetic field gradient within the magneto-optic film;
        an AC excitation coil located on a surface of the magneto-optic film; and
    an analyzer having a photodetector adapted to receive a reflected light signal passing through the magneto-optic film; the analyzer detecting angular rotated, linear displaced or deformed surfaces on the magnetic or non-magnetic surface by detecting changes in the reflected light signal from those of an unmoved or undeformed surface.

2. The magneto-optic sensor of claim 1 wherein the magneto-optic film comprises magneto-optic garnet film.

3. The magneto-optic sensor of claim 1 wherein the at least two permanent magnets comprises at least two hard ferrite permanent magnets.

4. The magneto-optic sensor of claim 3 wherein the at least two hard ferrite permanent magnets generate a uniform magnetic field gradient such that a stable two-domain structure with opposite directions of magnetization and a single domain wall is formed in the magneto-optic film.

5. The magneto-optic sensor of claim 1 wherein the at least one magneto-optic polarizer changer is located in the path of the reflected light such that the incident light beam does not pass through the at least one magneto-optic polarizer changer.

6. The magneto-optic sensor of claim 5 wherein another of the at least one magneto-optic polarizer changer is located in the path of the incident light beam.

7. The magneto-optic sensor of claim 1 wherein the at least one magneto-optic polarizer changer is located in the path of the reflected light and the incident light beam.

8. The magneto-optic sensor of claim 1 wherein the polarized light beam source is a laser.

9. The magneto-optic sensor of claim 8 wherein the laser is a He—Ne laser.

10. The magneto-optic sensor of claim 1 wherein the magnetic field gradient is larger than a pinning field of the magneto-optic film.

11. A method using the magneto-optic sensor of claim 1 to detect surface deformations on a magnetic or non-magnetic surface, wherein the at least two permanent magnets generate a uniform magnetic field gradient such that a stable two-domain structure with opposite directions of magnetization and a single domain wall is formed in the magneto-optic film, the method comprising the steps of:
   exciting the AC excitation coil at a predetermined frequency resulting in a periodically modulated output signal;
   passing the reflected light from the magnetic surface or non-magnetic surface through the magneto-optic film; and
   detecting temporal changes in the periodically modulated output signal indicative of a surface deformation.

12. The method of claim 11 further comprising the step of passing the incident light beam through the magneto-optic film and wherein the step of detecting temporal changes in the periodically modulated output signal comprises detecting changes in a width of a flat region in the periodically modulated output signal relative of the rest of the periodically modulated output signal.

13. The method of claim 11 wherein the step of exciting the AC excitation coil at a predetermined frequency comprises exciting the AC excitation coil with a periodic function.

14. The method of claim 13 wherein the step of exciting the AC excitation coil with a periodic function comprises the step of exciting the AC excitation coil with one of a sinusoidal function or a sawtooth function.

15. The method of claim 13 wherein the step of exciting the AC excitation coil with a periodic function generates a magnetic field perpendicular to a surface of the magneto-optic film.

16. The method of claim 11 wherein the step of detecting temporal changes in the periodically modulated output signal indicative of a surface deformation comprises detecting temporal changes in the periodically modulated output signal indicative of a angular rotated surface.

17. The method of claim 11 wherein the step of detecting temporal changes in the periodically modulated output signal indicative of a surface deformation comprises detecting temporal changes in the periodically modulated output signal indicative of a linear displaced surface.

18. The method of claim 11 further comprising the step of positioning the at least one magneto-optic polarizer changer at a position such that the reflected light from the magnetic surface or non-magnetic surface passes through the magneto-optic film.

19. The method of claim 18 further comprising the step of beaming incident light at the magnetic or non-magnetic surface at an angle such that reflected light passes through the magneto-optic film under all operating conditions.

* * * * *